United States Patent [19]

Dolgin

[11] Patent Number: 5,207,686
[45] Date of Patent: May 4, 1993

[54] SURGICAL SNARE

[76] Inventor: Stuart Dolgin, 95 Belvedere Dr., Syossett, N.Y. 11791

[21] Appl. No.: 869,522

[22] Filed: Apr. 15, 1992

[51] Int. Cl.⁵ .................. A61B 17/00; A61B 19/00
[52] U.S. Cl. ............................. 606/113; 606/1; 606/110; 606/45; 606/47; 606/49
[58] Field of Search ................. 606/110–113, 606/127, 128, 45–52, 1

[56] References Cited

U.S. PATENT DOCUMENTS

| | | | |
|---|---|---|---|
| 2,054,149 | 9/1936 | Wappler | 606/113 |
| 3,791,387 | 2/1974 | Itoh . | |
| 3,805,791 | 4/1974 | Seuberth et al. | 606/47 |
| 3,828,790 | 8/1974 | Curtiss et al. | 606/113 |
| 3,949,756 | 4/1976 | Ace . | |
| 4,010,756 | 3/1977 | DuMont et al. . | |
| 4,202,338 | 5/1980 | Bitrolf | 606/47 |
| 4,326,530 | 4/1982 | Fleury | 606/47 |
| 4,718,419 | 1/1988 | Okada | 606/47 |
| 4,905,691 | 3/1990 | Rydell | 606/47 |
| 5,084,054 | 1/1992 | Bencini et al. | 606/113 |
| 5,123,906 | 6/1992 | Kelman | 606/113 |

Primary Examiner—Stephen C. Pellegrino
Assistant Examiner—Glenn Dawson
Attorney, Agent, or Firm—Darby & Darby

[57] ABSTRACT

The wire loop of a surgical snare is constructed so as to include a weakened or frangible region. When it is desired to open the loop so as to move it from its entrapped position on a polyp, an additional force is exerted on the loop to draw it further into the sheath. This causes the frangible region to break, thereby opening the loop and permitting the wire to slide free of the polyp. In accordance with an alternate embodiment, the wire loop is constructed so as to fold back on itself, with the folded back end being captured by a retaining element inside the sheath. When the loop becomes entrapped on a polyp, it is extended out of the sheath somewhat further than during normal use, at which point the captured end of the loop is released, opening the loop and permitting its removal from within the patient.

2 Claims, 2 Drawing Sheets

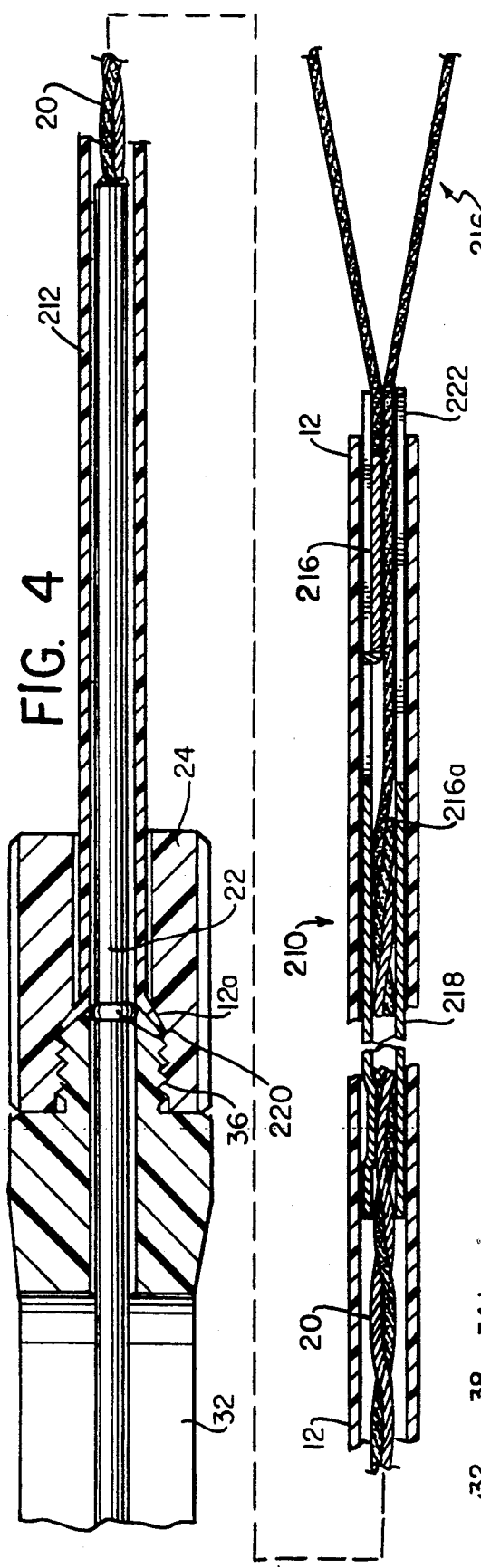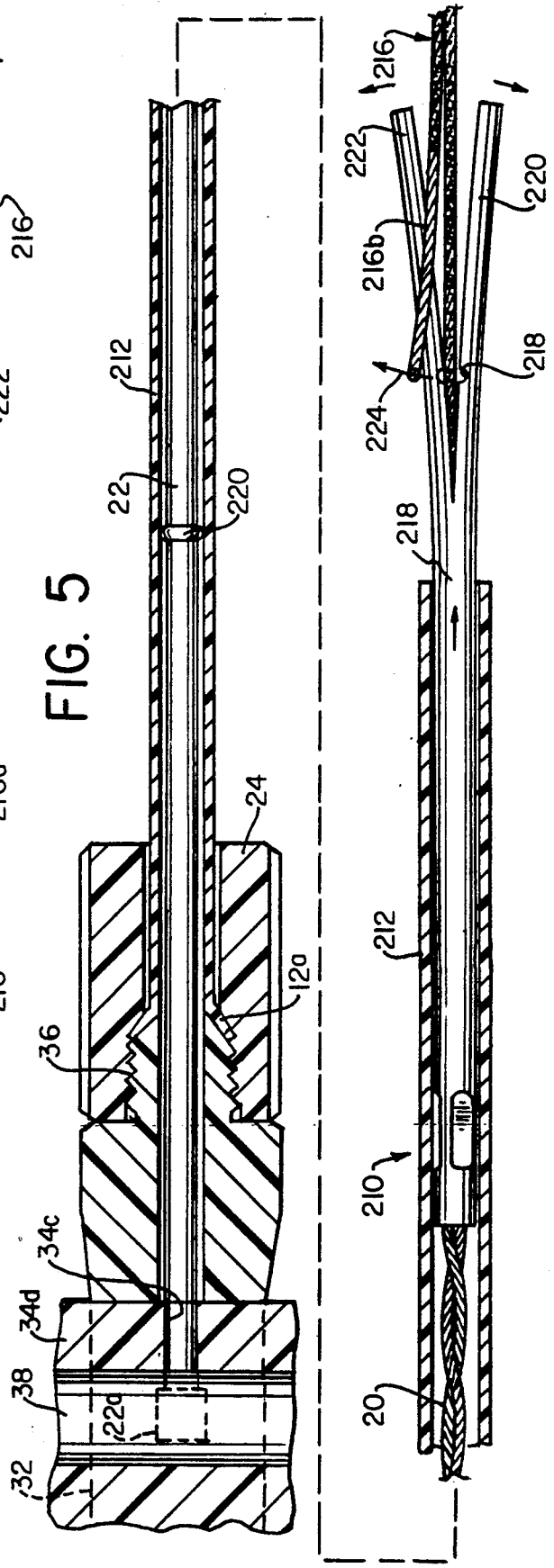

SURGICAL SNARE

FIELD OF THE INVENTION

The present invention relates generally to surgical snares and, more particularly, concerns such a snare in which the operative wire loop may be selectively opened during use.

BACKGROUND OF THE INVENTION

Surgical snares are commonly utilized to remove polyps which grow on the colon. A surgical procedure called a polypectomy, is performed after the surgeon has inserted a fiberoptic colonoscope to observe the inside lining of the colon. A surgical snare which has a wire loop that is slidably housed in a sheath is inserted into the patient through the colonoscope. The surgeon may then observe through this colonoscope as the snare is extended from the sheath and maneuvered so as to encircle the polyp. The wire loop is then withdrawn into the sheath until it is closed somewhat tightly around the stem of the polyp, at which time an electric current is passed through the wire loop. Through the resulting heating of the wire loop, the polyp is then cut from the lining of the intestine and removed from the patient with a different instrument.

On occasion, complications occur during a polypectomy. One such complication is that the polyp may have a particularly thick stem, and the heated loop is unable to cut completely through it. The surgeon may attempt to loosen the wire loop and to reposition it. However, at times the wire loop itself is caught in the polyp stem tissue and cannot be released from it. When the surgeon is not able to cut through the polyp or release the wire loop from its entrapped position on the polyp stem, the patient must be taken to surgery for the removal of the polyp and the wire snare.

It is an object of the present invention to avoid the shortcomings of existing surgical snares. It is specifically contemplated that a surgical snare in accordance with the present invention be capable of being operated so that the wire scoop can be selectively opened to permit ready removal of the surgical snare in the event it becomes entrapped on a polyp.

It is also an object of the present invention to provide a surgical snare with a releasable loop which is relatively simple and inexpensive in construction, yet reliable and convenient in use.

In accordance with a preferred embodiment demonstrating objects and features of the present invention, a wire loop of a surgical snare is constructed so as to include a weakened or frangible region. When it is desired to open the loop so as to move it from its entrapped position on a polyp, an additional force is exerted on the loop to draw it further into the sheath. This causes the frangible region to break, thereby opening the loop and permitting the wire to slide free of the polyp.

In accordance with a second embodiment of the invention, a wire loop is constructed so as to fold back on itself, with the folded back end being captured inside the sheath. When the loop becomes entrapped on a polyp, it is extended out of the sheath somewhat further than during normal use, at which point the captured end of the loop is released, opening the loop and permitting its removal from within the patient.

BRIEF DESCRIPTION OF THE DRAWINGS

The foregoing brief description, as well as further objects, features, and advantages of the present invention will be understood more completely from the following detailed description of presently preferred, but nonetheless illustrative, embodiments of the present invention, with reference being had to the accompanying drawings in which:

FIG. 4 is lengthwise sectional view of a second embodiment of a surgical snare in accordance with the present invention, showing the internal construction thereof with the snare in its position of normal use; and FIG. 5 is a sectional view similar to FIG. 4, showing the surgical snare after it has been operated so as to open the wire loop.

DETAILED DESCRIPTION OF THE PREFERRED EMBODIMENTS

Figure 1:
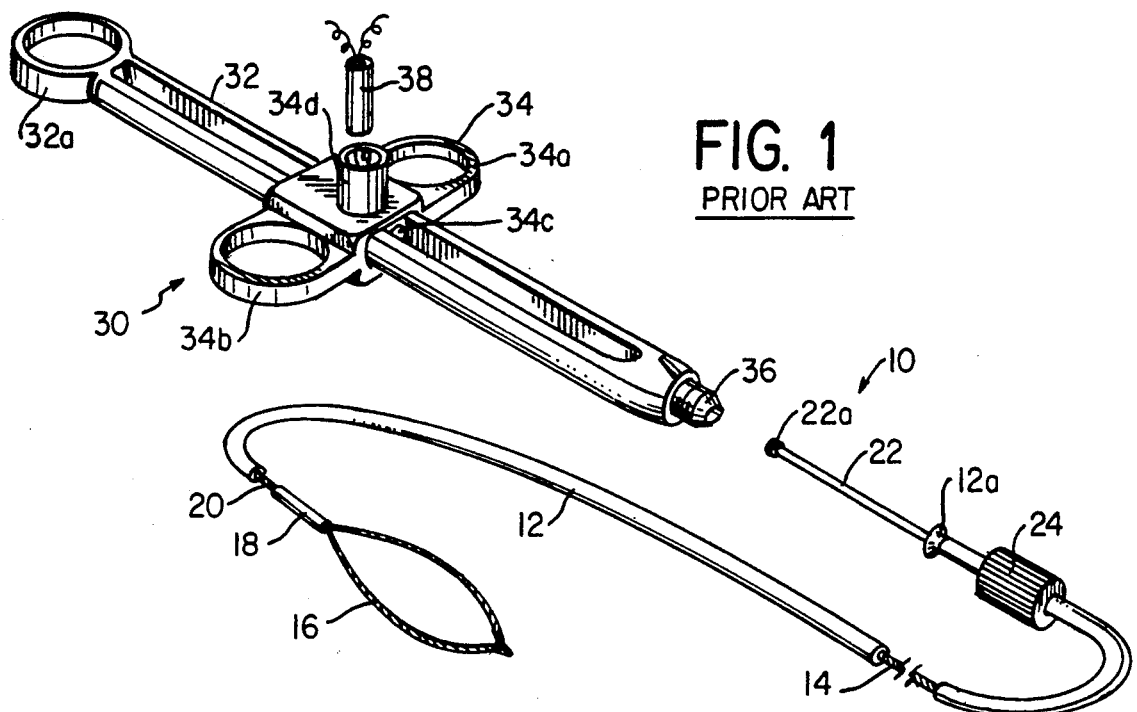
FIG. 1 is a perspective view showing a conventional, surgical snare and its operating handle.

FIG. 1 illustrates a conventional surgical snare 10 which includes an external sheath 12 and a wire assembly 14 which is slidably received within the sheath 12. The sheath is shown partially cut away to aid the disclosure. Wire assembly 14 includes a wire loop 16 which is held together by a ferrule 18. The wire end forming loop 16 are then twisted together (e.g. at 20), which adds stiffness to the wire assembly and facilitates its sliding within the sheath 12. At the end of wire assembly 14 which is opposite loop 16, the wires exit the sleeve 12 and pass into a stiffening sleeve, which terminates in a connecting lug 22a. Sheath 12 includes an end cap 24, which is used to connect snare 10 to an operating handle 30.

The operating member 30 has a stationary element 32 and a sliding element 34 mounted on the stationary element. The stationary element has a finger hole 32a, in which the user normally places his thumb and the sliding element 34 has two finger holes 34a and 34b into which the user places his first and second fingers. The end of member 30 opposite finger hole 32a, indicated by the reference character 36, is shaped to engage the end 12a of sheath 12 and is adapted to mate with cap 24, as by complementary internal and external threads. Sliding member 34 includes an opening 34c into which the end 22a of snare 10 may be received for mechanical and electrical connection. Sliding element 34 would also include some sort of a release button or lever (not shown) to permit removal of the end 22a from the sliding element. In addition element 34 includes an electrical connector 34d, which can receive the connection wire 38 from a cautery machine.

In operation, the portion 22 of snare 10 is inserted into end 36 of member 30 and into opening 34c of element 34, wherein it is mechanically engaged. End 12a of sheath 12 is then placed in contact with the tip of end 36 of member 30, and cap 24 is screwed onto member 30 to secure the sheath to element 32. The operator may then use his thumb and first two fingers of one hand to slide element 34 on element 32, whereby wire assembly 14 is slidingly moved within sheath 12 and can be utilized in the manner described above.

The cautery machine can be operated so as to cause current to flow into the wire assembly 14 and around loop 16. It will be appreciated that in order to permit such current flow around loop 16 and prevent a short circuit at section 20, the wire must be insulated from member 30 to ferrule 18.

Figure 2:
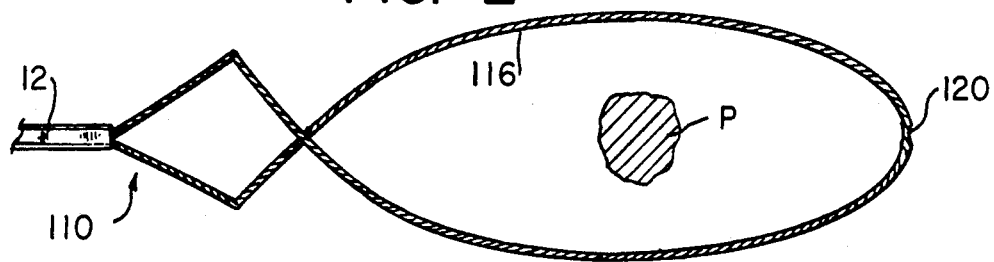
FIG. 2 is a fragmentary view, on an enlarge scale, showing a surgical snare in accordance with a first embodiment of the present invention applied over a polyp.

FIG. 2 is a fragmentary view showing a first embodiment 110 of a surgical snare in accordance with the present invention positioned over the stem of a polyp P. Except as specifically discussed below, the construction of the surgical snare 110 is identical to surgical snare 10 of FIG. 1. Details of surgical snare 110 have therefore been omitted, except to the extent that it differs from snare 10. Wire loop 116 of snare 110 is formed with a reduced, weakened or frangible region 120, which may be positioned at any point along the loop, but is preferably at the outermost tip of the loop. Once the loop 116 is positioned over the stem of the polyp P, element 34 of member 30 is pulled toward hole 32a whereby the loop 116 is drawn into the sheath 12. Eventually, loop 116 is drawn tightly around the stem of the polyp (shown in dotted lines in FIG. 3). At this time, an electric current would be provided to loop 116 via the cautery machine, in order to sever the polyp.

Figure 3:
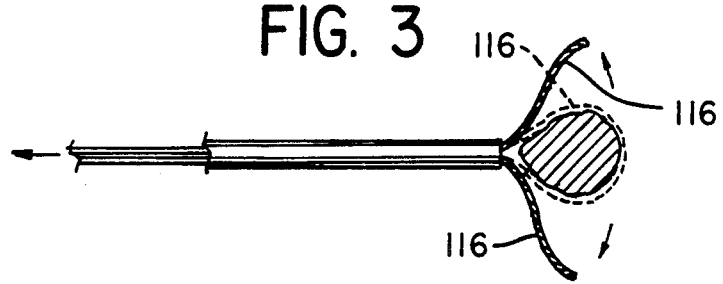
FIG. 3 is a fragmentary view similar to FIG. 2 showing the surgical snare of FIG. 2 after it has been tightened about the polyp stem and operated so as to open the wire loop.

Should the wire 116 become stuck to the polyp so that it cannot be removed by opening up loop 116, it is only necessary to apply an additional force to element 34, which causes loop 116 to break at weakened region 120 (shown in solid lines in FIG. 3), whereby further force applied to element 34 causes the severed parts of loop 116 to be pulled away from the polyp and withdrawn into the sheath, as indicated by the arrows at the right in FIG. 3 and the single arrow at the left in FIG. 3.

FIG. 4 is an alternate embodiment 210 of a surgical snare in accordance with the present invention. With the exception of the differences discussed below, snare 210 is identical to snare 10 of FIG. 1. The primary distinction is that ferrule 218 is constructed somewhat differently than ferrule 18. It is assumed that wire forming loop 216 has an insulated coating where the two portions of the wire come into contact with each other. Essentially, the entire wire forming the loop 216 and the portions extending back to the electrical connection to the cautery is a single wire looping back on itself. Within ferrule 218, one portion of this wire is cut and the two resulting ends 216a and 216b are stripped of insulating material. In addition, end 216b is formed with an L-shaped hook, which extends into a hole 218a formed in ferrule 218. Those skilled in the art will appreciate that end 216b may be alternately constructed and still achieve the same operation. For example, it could be formed with a ball at the end 216b dimensioned to similarly extend into hole 218a.

Ferrule 218 is preferably made of metal, it may be made of any other resilient material, so long as its interior surface is coated or otherwise treated so as to be electrically conductive. As a result of this electrical conductivity, ferrule 218 provides an electrical connection between ends 216a and 216b whereby current can flow through loop 216. As best seen in FIG. 5, ferrule 218 is longitudinally split into two diametrically opposed halves 220 and 222. As long as the wire assembly is positioned so that hole 218a is within sheath 212, the two halves 220 and 222 will be pressed together and loop 216 will remain closed. However, should ferrule 218 be extended sufficiently forwardly out of sheath 212, halves 220 and 222 will spring apart (indicated by the arrows at the right of FIG. 5) as a result of the resilience of ferrule 218. This causes hole 218a to be opened, whereby the end 216b comes free of ferrule 218 (indicated by the arrow 224). Member 30 may then be operated as explained previously to withdraw ferrule 218 into sheath 212 and loop 216 will follow, since end 216b is now free.

In order to facilitate proper operation of snare 210, appropriate markings may be provided on element 32 to assure that element 34 is not brought too far forward. It is to be appreciated that, in normal operation, ferrule 18 should always remain within the sheath 212. Accordingly, a forward portion of element 32 may be colored red and the operator instructed that element 34 should not be brought into the red region unless it is desired to disengage loop 216.

Alternatively, portion 22 of snare 110 could be formed with a protrusion 220 which would have a relatively snug fit within sheath 12 but a relatively loose fit outside that sheath. Protrusion 220 is positioned so as to be just outside sheath 12 when ferrule 218 just begins to protrude from the sheath (see FIG. 4). Further extension of ferrule 218 out of the sheath would therefore force protrusion 220 into the interior of the sheath, at which time the operator would feel an increased resistance to movement. The operator would then be aware that further extension of the snare out of sheath 12 would cause the loop 216 to open (see FIG. 5). Protrusion 220 could be formed integrally on section 22 or, preferably, it could be resilient a washer which is positioned on section 22 and held in place by a bonding material or its own resilient force.

Although preferred forms of the invention have been disclosed for illustrative purposes, those skilled in the art would appreciate that many additions, modifications, and substitutions are possible without departing from the scope and spirit of the invention as defined in the accompanying claims.

What is claimed is:

1. In a surgical snare of the type including a sheath and a wire assembly slidably mounted within the sheath, the wire assembly being moved within the sheath as a result of its being manipulated by a user at a near end thereof, the wire assembly being formed into a loop at a distal end thereof, the improvement comprising means responsive to the manipulation of the near end by the user for causing said loop to become discontinuous, whereby the snare may be removed from a patient when the loop becomes caught on a polyp, said wire loop being formed by doubling an end of the wire back on itself, said means for causing said loop to become discontinuous comprising releasable connecting means for providing an electrical and mechanical connection between said wire loop end and another portion of said wire assembly, including means for releasing said connection in response to said wire assembly being manipulated to slide within said sheath so as to expand out of said sheath beyond a predetermined distance.

2. The surgical snare of claim 1 further comprising means for producing resistance to relative sliding movement between said wire assembly and said sheath when said wire loop approaches said predetermined distance, whereby a user is provided an indication of impending release of said loop.

* * * * *

UNITED STATES PATENT AND TRADEMARK OFFICE
CERTIFICATE OF CORRECTION

PATENT NO. : 5,207,686

DATED : May 4, 1993

INVENTOR(S) : Stuart Dolgin

It is certified that error appears in the above-identified patent and that said Letters Patent is hereby corrected as shown below:

The title page, should be deleted to appear as per attached title page.

Signed and Sealed this

Twentieth Day of September, 1994

Attest:

BRUCE LEHMAN

Attesting Officer

Commissioner of Patents and Trademarks

United States Patent [19]

Dolgin

[11] Patent Number: 5,207,686
[45] Date of Patent: May 4, 1993

[54] SURGICAL SNARE

[76] Inventor: Stuart Dolgin, 95 Belvedere Dr., Syossett, N.Y. 11791

[21] Appl. No.: 869,522

[22] Filed: Apr. 15, 1992

[51] Int. Cl.⁵ .................. A61B 17/00; A61B 19/00
[52] U.S. Cl. ............................. 606/113; 606/1; 606/110; 606/45; 606/47; 606/49
[58] Field of Search ................... 606/110–113, 606/127, 128, 45–52, 1

[56] References Cited

U.S. PATENT DOCUMENTS

| | | | |
|---|---|---|---|
| 2,054,149 | 9/1936 | Wappler | 606/113 |
| 3,791,387 | 2/1974 | Itoh | |
| 3,805,791 | 4/1974 | Seuberth et al. | 606/47 |
| 3,828,790 | 8/1974 | Curtiss et al. | 606/113 |
| 3,949,756 | 4/1976 | Ace | |
| 4,010,756 | 3/1977 | DuMont et al. | |
| 4,202,338 | 5/1980 | Bitrolf | 606/47 |
| 4,326,530 | 4/1982 | Fleury | 606/47 |
| 4,718,419 | 1/1988 | Okada | 606/47 |
| 4,905,691 | 3/1990 | Rydell | 606/47 |
| 5,084,054 | 1/1992 | Bencini et al. | 606/113 |
| 5,123,906 | 6/1992 | Kelman | 606/113 |

Primary Examiner—Stephen C. Pellegrino
Assistant Examiner—Glenn Dawson
Attorney, Agent, or Firm—Darby & Darby

[57] ABSTRACT

The wire loop of a surgical snare is constructed so as to include a weakened or frangible region. When it is desired to open the loop so as to move it from its entrapped position on a polyp, an additional force is exerted on the loop to draw it further into the sheath. This causes the frangible region to break, thereby opening the loop and permitting the wire to slide free of the polyp. In accordance with an alternate embodiment, the wire loop is constructed so as to fold back on itself, with the folded back end being captured by a retaining element inside the sheath. When the loop becomes entrapped on a polyp, it is extended out of the sheath somewhat further than during normal use, at which point the captured end of the loop is released, opening the loop and permitting its removal from within the patient.

2 Claims, 2 Drawing Sheets

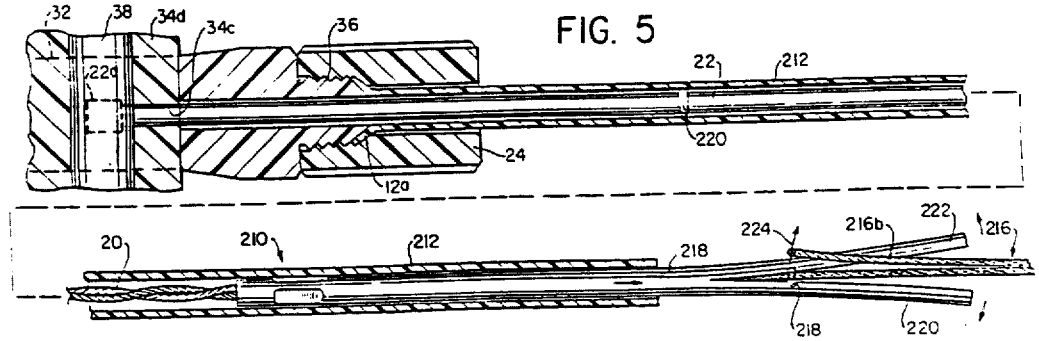

FIG. 5

UNITED STATES PATENT AND TRADEMARK OFFICE
CERTIFICATE OF CORRECTION

PATENT NO. : 5,207,686

DATED : May 4, 1993

INVENTOR(S) : Stuart Dolgin

It is certified that error appears in the above-identified patent and that said Letters Patent is hereby corrected as shown below:

The title page, should be deleted to appear as per attached title page.

Signed and Sealed this

Eighth Day of August, 1995

Attest:

BRUCE LEHMAN

*Attesting Officer*  *Commissioner of Patents and Trademarks*

United States Patent [19]

Dolgin

[11] Patent Number: 5,207,686
[45] Date of Patent: May 4, 1993

[54] SURGICAL SNARE

[76] Inventor: Stuart Dolgin, 95 Belvedere Dr., Syossett, N.Y. 11791

[21] Appl. No.: 869,522

[22] Filed: Apr. 15, 1992

[51] Int. Cl.⁵ .................. A61B 17/00; A61B 19/00
[52] U.S. Cl. .................................... 606/113; 606/1; 606/110; 606/45; 606/47; 606/49
[58] Field of Search ................. 606/110–113, 606/127, 128, 45–52, 1

[56] References Cited

U.S. PATENT DOCUMENTS

| | | | |
|---|---|---|---|
| 2,054,149 | 9/1936 | Wappler | 606/113 |
| 3,791,387 | 2/1974 | Itoh . | |
| 3,805,791 | 4/1974 | Seuberth et al. | 606/47 |
| 3,828,790 | 8/1974 | Curtiss et al. | 606/113 |
| 3,949,756 | 4/1976 | Ace . | |
| 4,010,756 | 3/1977 | DuMont et al. . | |
| 4,202,338 | 5/1980 | Bitrolf | 606/47 |
| 4,326,530 | 4/1982 | Fleury | 606/47 |
| 4,718,419 | 1/1988 | Okada | 606/47 |
| 4,905,691 | 3/1990 | Rydell | 606/47 |
| 5,084,054 | 1/1992 | Bencini et al. | 606/113 |
| 5,123,906 | 6/1992 | Kelman | 606/113 |

Primary Examiner—Stephen C. Pellegrino
Assistant Examiner—Glenn Dawson
Attorney, Agent, or Firm—Darby & Darby

[57] ABSTRACT

The wire loop of a surgical snare is constructed so as to include a weakened or frangible region. When it is desired to open the loop so as to move it from its entrapped position on a polyp, an additional force is exerted on the loop to draw it further into the sheath. This causes the frangible region to break, thereby opening the loop and permitting the wire to slide free of the polyp. In accordance with an alternate embodiment, the wire loop is constructed so as to fold back on itself, with the folded back end being captured by a retaining element inside the sheath. When the loop becomes entrapped on a polyp, it is extended out of the sheath somewhat further than during normal use, at which point the captured end of the loop is released, opening the loop and permitting its removal from within the patient.

2 Claims, 2 Drawing Sheets

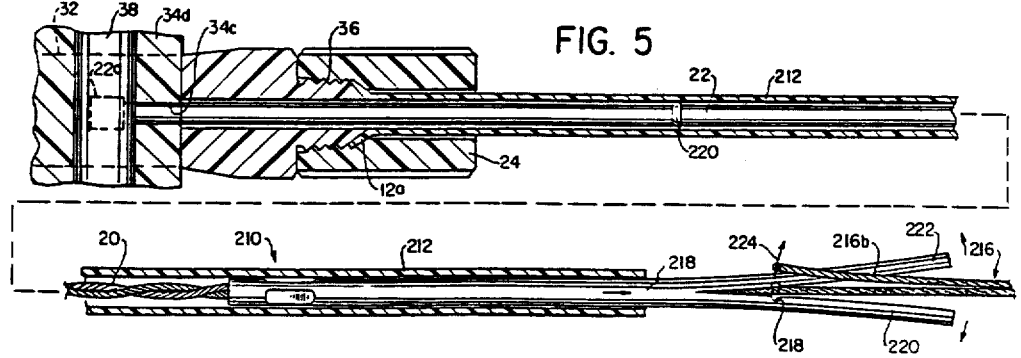

FIG. 5